US008916214B2

(12) United States Patent
Moonen et al.

(10) Patent No.: US 8,916,214 B2
(45) Date of Patent: Dec. 23, 2014

(54) PROCESS FOR PREPARING A FREE-FLOWING POWDER CONTAINING A DELIQUESCENT QUATERNARY AMMONIUM COMPOUND

(75) Inventors: Kristof Moonen, Hamme (BE); Daan Scheldeman, Waregem (BE)

(73) Assignee: Taminco N.V., Ghent (BE)

( * ) Notice: Subject to any disclaimer, the term of this patent is extended or adjusted under 35 U.S.C. 154(b) by 362 days.

(21) Appl. No.: 13/141,871

(22) PCT Filed: Dec. 24, 2009

(86) PCT No.: PCT/EP2009/067926
§ 371 (c)(1),
(2), (4) Date: Aug. 5, 2011

(87) PCT Pub. No.: WO2010/072842
PCT Pub. Date: Jul. 1, 2010

(65) Prior Publication Data
US 2011/0287140 A1 Nov. 24, 2011

(30) Foreign Application Priority Data
Dec. 24, 2008 (EP) .................................. 08172900

(51) Int. Cl.
```
A23L 1/30      (2006.01)
A23K 1/175     (2006.01)
A23C 9/12      (2006.01)
A61K 9/50      (2006.01)
A23D 7/00      (2006.01)
A23D 9/00      (2006.01)
A23C 15/14     (2006.01)
A61K 9/16      (2006.01)
A23K 1/00      (2006.01)
A23L 1/304     (2006.01)
A23L 2/52      (2006.01)
```
(52) U.S. Cl.
CPC ............... *A23K 1/002* (2013.01); *A61K 9/1617* (2013.01); *A23L 1/304* (2013.01); *A23K 1/1758* (2013.01); *A23L 2/52* (2013.01); *A23V 2002/00* (2013.01); *A23L 1/3045* (2013.01)

USPC ............... 426/74; 426/61; 426/417; 426/601; 424/498; 424/502

(58) Field of Classification Search
CPC .. A23L 1/304; A23L 1/3045; A23V 2002/00; A23K 1/1758; A61K 9/5105; A61K 9/1617; A61K 9/1652; A61K 9/5084; A61K 9/0056
USPC ............... 426/61, 74, 601, 417; 424/498, 502
See application file for complete search history.

(56) References Cited

U.S. PATENT DOCUMENTS 5,486,363 A     1/1996   Kiefer et al.
5,766,668 A *   6/1998   Brommelsiek et al. ........ 426/648

FOREIGN PATENT DOCUMENTS

GB     1161970 A       8/1969
GB     1161970 A *    2/1970
WO    96/29886 A2    10/1996

OTHER PUBLICATIONS

"Sodium Stearate" Hawley's Condensed Chemical Dictionary, 14th Edition (2002).*
"Agglomeration/Granulation" Available online at www.cjtech.co.kr on Aug. 3, 2004.*
21 CFR 573.280—Feed-grade calcium stearate and sodium stearate. (1998).*
International Search Report of PCT/EP2009/067926 dated Feb. 23, 2010.

* cited by examiner

*Primary Examiner* — Rena L Dye
*Assistant Examiner* — Assaf Zilbering
(74) *Attorney, Agent, or Firm* — Sughrue Mion, PLLC

(57) ABSTRACT

A process is described for obtaining free flowable, carrier free powders from aqueous solutions of deliquescent quaternary ammonium compounds in a two step process, comprising a drying and a powder mixing step. The excellent free-flowing and stability characteristics of the final product could only be obtained when among possible other additives at least one univalent metal fatty acid salt is added to the liquid phase in the drying step and at least one multivalent metal fatty acid salt in the powder mixing step. A surprising synergy was observed between these additives when applied as described in the present invention.

20 Claims, No Drawings

PROCESS FOR PREPARING A FREE-FLOWING POWDER CONTAINING A DELIQUESCENT QUATERNARY AMMONIUM COMPOUND

CROSS REFERENCE TO RELATED APPLICATIONS

This application is a National Stage of International Application No. PCT/EP2009/067926 filed Dec. 24, 2009, claiming priority based on European Patent Application No. 08172900.6, filed Dec. 24, 2008, the contents of all of which are incorporated herein by reference in their entirety.

The present invention relates to a process for preparing a free-flowing powder containing, on a dry weight basis, per 100 parts by weight, at least 85 parts by weight, preferably at least 90 parts by weight and more preferably at least 95 parts by weight of at least one deliquescent quaternary ammonium compound. The free-flowing powder is prepared by drying an aqueous solution of the quaternary ammonium compound to achieve a solid product and by subsequently admixing at least one powdery salt of a medium to long chain fatty acid with a multivalent counter ion to this solid product in an amount of at least 0.1 part by weight per 100 parts by weight of the quaternary ammonium compound.

Quaternary ammonium compounds, including betaines, are often deliquescent compounds, i.e. powdery materials (obtained in pure form through for example crystallization or drying) that readily absorb water from the ambient atmosphere to such an extent that liquefaction occurs spontaneously. The rate at which this process (from dry phase to liquid phase) occurs is depending on the individual compound, but the intermediate stages always show aggregating and sticking powders that are not easily handled. Therefore, carrier materials often are required to stabilize the product during the application resulting in reduced active ingredient concentration and hard to control product safety.

Choline chloride, for instance, is used on a large scale in the animal feed industry as a feed additive. Usually, vitamins and trace elements are added to the animal feed as a premix in dry form. Choline chloride, however, is often produced as a 75% aqueous solution. Anhydrous samples obtained through crystallization absorb moisture very fast from ambient air and become sticky. Therefore, choline chloride is sold in practice in a solid form for application in animal feed after absorption on silica or minced vegetable material as a carrier. In this way, the choline chloride content of these products is, however, generally limited to 70%. Moreover, when cheaper minced vegetable material is used as a carrier, the exact chemical composition and contamination level of the vegetable carrier is often difficult to control while it actually is of utmost importance for food and feed safety.

A process wherein silica is used as a carrier is disclosed for example in U.S. Pat. No. 4,775,540. In this process a relatively large amount of silica is added to a 70 to 80% choline chloride solution so that the choline chloride concentration is reduced to 40 to 50 wt. %. Since the pourability of the thus obtained powdered mixture is still inadequate, 0.05 to 0.4 wt. % of magnesium stearate or calcium stearate are admixed thereto. The resulting powder could be poured through an orifice of 5 mm and could still be poured through an orifice of 20 mm after 24 hours standing in air at 75% relative humidity. A drawback of this process is that relatively large amounts of silica are required so that the obtained product has only a limited choline chloride content.

Instead of adding silica to the choline chloride solution, it is also known to add sodium stearate thereto. Such a process is disclosed in NL 6704009. In this known process, 25 parts by weight of sodium stearate are added to a 70 wt. % choline chloride solution per 100 parts by weight of choline chloride. In this way a suspension is obtained which is subsequently dried. According to NL 6704009 drying of this suspension can be done by drum drying or by spray drying. However, only examples of a drum drying process are given. Due to the high content of suspended solid sodium stearate particles in the choline chloride solution, this solution is in fact not suitable at all for being spray dried (see for example the examples of U.S. Pat. No. 6,177,124 mentioning that a 75% choline chloride solution containing only 3.8% of silica may already be too viscous to be atomized in a spray drier). Moreover, it appears from NL 6704009 that when spray drying the suspension, a solid product would be obtained which has to be milled to achieve a powder. Nothing is mentioned in NL 6704009 about the stability of the dried powder and about how its free-flowing properties are evaluated. From a comparative test carried out by the present inventors (see comparative example 7), it appears that when spray drying a choline chloride solution containing stearates (a small amount of sodium and calcium stearates) suspended therein, a very lumpy material is indeed obtained, but, after milling this lumpy material, it still could not be poured through an orifice of 6 mm and had only a limited stability. A further comparative test (see comparative example 9d) showed that when drying and milling the suspension prepared in NL 6704009 the obtained dry product had some free-flowing properties but did not flow spontaneously through an orifice of 6 mm. Moreover, during a stability test wherein a thin layer of the dried and milled product was kept at 20° C. and at a relative humidity of 75%, the product became already sticky after 1 hour and clearly showed water droplets on the surface after 2 hours. Finally, the product obtained by the process disclosed in NL 6704009 has again a low choline chloride content and is relatively expensive due to the high amounts of sodium stearate which are needed.

A process which does enable to achieve a free-flowing powder having a high choline chloride content is disclosed in U.S. Pat. No. 6,177,124 and DE 2209477. These patent publications disclose the use of hydrophobic silica as an additive in solid choline chloride to prevent it from liquefying and to maintain sufficient free-flowing properties to guarantee easy handling. In this way, choline chloride can be obtained in a solid form having up to 95% active ingredient by spray drying an aqueous silica-choline chloride suspension. However, hydrophobic silica is very expensive and has a profound influence on the pricing of the end product.

U.S. Pat. No. 5,486,363 discloses a process wherein a dry, free-flowing choline chloride containing powder is again produced with the aid of hydrophobic silicic acid. Instead of admixing this hydrophobic silicic acid powder to the choline chloride solution, it is finely dispersed in a counter-current flowing air stream in the spray drying tower. A product with a high choline chloride content (containing only 2.7 wt. % $SiO_2$) could be obtained. However, to obtain a sufficiently dry powder, two step drying or tall form (20-30 m) spray dryers are required. U.S. Pat. No. 5,486,363 suggests also to use much cheaper fatty acid salts instead of the hydrophobic silica. However, no experimental data are given. The present inventors have done a test (see comparative example 8a) wherein they introduced such an amount of calcium stearate powder by means of an air flow in the drying chamber of a spray drying tower that the dried choline chloride contained 2.5 wt. % of calcium stearate. It appeared that the obtained product was not free-flowing, even not when admixing 1% of calcium stearate to the dried product, so that the process disclosed in U.S. Pat. No. 5,486,363 apparently only works with the aid of the much more expensive hydrophobic silica.

DD 84552 discloses a process for preparing a solid choline chloride product with a high choline chloride content wherein use is made of less expensive fatty acid salts. In this known process, a choline chloride solution is dried and a vacuum is applied to avoid or limit the absorption of moisture. Then, 0.5 to 10 parts, preferably 2 to 5 parts of calcium or magnesium stearate are mixed with the dried choline chloride. A problem with this known process is that the dried choline chloride is very hygroscopic and starts immediately to adhere to the cooler parts of the drying/cooling installation (see comparative example 6). The drying process can thus be carried out only for a limited period of time before the drying installation has to be cleaned. Moreover, although DD 84552 describes the production of a free-flowing product, it appears that the flowability still needs to be improved. Indeed, from the comparative example 8a referred to already hereabove, it appears that when spray drying a choline chloride solution and mixing the dried choline chloride with 1% of calcium stearate, the obtained product still did not flow through an orifice of 6 mm, notwithstanding the fact that during the spray drying step about 2.5% of calcium stearate was additionally added to the choline chloride.

An object of the present invention is to provide a new process which enables to produce a free-flowing powder (which can flow through an orifice with a diameter of only 6 mm) from a solution of a deliquescent quaternary ammonium compound, in particular from a choline chloride solution, without having to use expensive hydrophobic silica or large amounts of other additives or carriers so that the obtained powder has a relatively high content of the quaternary ammonium compound. The new process should also enable to avoid sticking of the deliquescent quaternary ammonium compound to the drying installation, especially when using a spray drying installation.

To achieve this object, the process according to the invention is characterised in that, before drying the aqueous solution of the deliquescent quaternary ammonium compound, at least one water-soluble salt of a medium to long chain fatty acid with a univalent counter ion is introduced therein, at least 0.1 part by weight of said water-soluble salt being dissolved in said aqueous solution, per 100 parts by weight of said quaternary ammonium compound.

After having dried the aqueous solution, a solid product is obtained to which, per 100 parts by weight of said quaternary ammonium compound, at least 0.1 part by weight of at least one powdery salt of a medium to long chain fatty acid with a multivalent counter ion is admixed.

The present inventors have found that when first dissolving an amount of a water-soluble fatty acid salt with a univalent counter ion in the aqueous solution and when admixing subsequently, after having dried the aqueous solution to a solid product, a powdery salt of a fatty acid with a multivalent counter ion to the obtained dry product, a free-flowing powder can be obtained with a smaller amount of fatty acid salts and with better free-flowing properties. In this respect, it should be noted that when describing in the present patent specification that the powder of the invention is free-flowing, this means that the powder flows by gravity through a round orifice with a diameter of only 6 mm.

Synergetic effects were found to occur between the fatty acid salt dissolved in the aqueous solution and the fatty acid salt mixed with the dried product, especially on the free-flowing properties of the obtained powder. To achieve these synergetic effects, it appeared to be essential that a minimum amount of the water-soluble fatty acid salt is actually dissolved in the aqueous solution. When adding a fatty acid salt which does not dissolve in water, such as for example calcium stearate, to the aqueous solution, a free-flowing powder could not be achieved by mixing the dried solid product subsequently with the powdery fatty acid salt (in particular with calcium stearate). However, when the aqueous solution contained only a relatively small amount of dissolved fatty acid salt, the free-flowing properties of the powder obtained by subsequently mixing the powdery fatty acid salt with the dried powder were considerably improved. Why this synergy occurs is not clear but a possible theory is that the fatty acid chains of the dissolved fatty acid salt migrate to the air-liquid intersurface so that they are concentrated at the surface of the dried particles (where they might form a very thin film) and interact there with the powdery fatty acid salt so as to increase the flowability of the powder. When the fatty acid salt particles are on the contrary not dissolved but only suspended in the aqueous solution, they remain more within the core of the product and cannot form a film at the surface of the powder particles.

In a preferred embodiment of the process according to the invention, the aqueous solution is heated to a temperature higher than 50° C., preferably higher than 60° C. and more preferably higher than 75° C. to dissolve said water-soluble salt therein.

The water-soluble fatty acid salt has only a limited solubility in water. By heating the aqueous solution more of the fatty acid salt can be dissolved therein. This is especially important for an aqueous solution having a higher content of the deliquescent quaternary ammonium compound since in such a solution the solubility of the fatty acid salt is even lower. In the process disclosed in NL 6704009, the aqueous solution which contains 70% choline chloride is on the contrary not heated so that, as described therein, a suspension is achieved when adding the sodium stearate thereto, wherein no or almost no sodium stearate is dissolved therein notwithstanding the large amount of sodium stearate added thereto.

The present invention also relates to the free-flowing powder obtained by the process according to the invention, and in particular to a free-flowing powder which remains free-flowing when stored in a thin layer of about 3 mm for 3 hours at 20° C. and at 75% relative air humidity.

The present invention further relates to a feed additive mixture comprising the free-flowing powder of the invention mixed with at least one further powder selected from the group consisting of vitamins, minerals, anti-oxidants, antimicrobial agents, anthelmintics, microbial supplements, oligosaccharides, enzymes, amino acids, acidifiers, flavors, odor control agents, pellet binders, flow agents, fats, carotenoids and carcass modifiers.

Further particularities and advantages of the invention will become apparent from the following more detailed description of the process, the free-flowing powder and the feed additive mixture according to the present invention.

The invention relates to a process for preparing a free-flowing powder containing, on a dry weight basis, per 100 parts by weight of the powder, at least 85 parts by weight, preferably at least 90 parts by weight and more preferably even at least 95 parts by weight of at least one deliquescent quaternary ammonium compound.

The term deliquescent compound refers to those compounds that absorb water from the ambient atmosphere (at a temperature of 20° C. and a relative humidity of 75%) to such an extent that liquefaction occurs before the equilibrium water content is attained. Quaternary ammonium compounds are those organic molecules that contain at least one nitrogen atom that is bonded to four carbon atoms and hence carries a positive charge. As a counter ion, organic as well as inorganic anions can occur, exemplified but not limited by halogenides, carboxylates, carbonates, sulphates or hydroxide. Betaines are known as a special class of quaternary ammonium compounds carrying both the positive charge (ammonium nitrogen atom) and negative charge (carboxylate oxygen atom) in the same molecule. Examples of deliquescent quaternary ammonium compounds, including betaines, that are advantageously treated under the conditions of the present invention include choline species (choline chloride, bromide, hydroxide, carboxylate, carbonate), glycine betaine, tetramethylammonium chloride & bromide, D,L-carnitine, etc. . . . .

As mentioned already hereabove, the term "free-flowing powder" refers to a powder that can flow by gravity through a round orifice which has a diameter of only 6 mm.

To prepare the free-flowing powder, use is made of an aqueous solution of the deliquescent quaternary ammonium salt. This solution is dried to achieve a dried solid product. In order to reduce the drying capacity which is required for this drying step, the aqueous solution preferably contains more than 50 wt. %, preferably more than 60 wt. % and more preferably more than 70 wt. % of the quaternary ammonium salt.

The drying step can be carried out in different ways which can be divided in two main categories, namely contact drying and convective drying (by means of drying air). Contact drying techniques include hot plate drying and drum drying whilst convective drying techniques include fluidized bed drying, flash drying and spray drying which includes spray granulation and spray agglomeration.

An essential feature of the process of the present invention is that, before drying the aqueous solution, at least one water-soluble salt of a medium to long chain fatty acid with a univalent counter ion is introduced therein and at least 0.1 part by weight of this water-soluble salt is actually dissolved in the aqueous solution, per 100 parts by weight of the deliquescent quaternary ammonium compound. The amount of the water-soluble salt introduced in the aqueous solution is preferably smaller than 10 parts by weight, more preferably less than 5 parts by weight and most preferably less than 3 parts by weight per 100 parts by weight of said quaternary ammonium compound. In fact, the water-soluble salt has only a limited solubility in water so that when adding too much, a portion thereof will remain in suspension. Since this increases the viscosity of the aqueous solution, problems may arise especially when drying the solution by techniques wherein the solution has to be atomised. Moreover, the portion of the water-soluble salt which would remain suspended in the solution reduces also the concentration of the ammonium compound in the final product substantially without contributing to the free-flowing properties thereof. Consequently, preferably more than 20%, more preferably more than 50% and most preferably more than 75% of the water-soluble salt introduced in the aqueous solution is dissolved therein before drying the solution.

In order to be able to dissolve more of the water-soluble salt, the aqueous solution is preferably heated, in particular to a temperature higher than 50° C., preferably higher than 60° C. and more preferably higher than 75° C. Preferably, at least 0.2 parts by weight, more preferably at least 0.3 parts by weight and most preferably at least 0.4 parts by weight of said water-soluble salt is dissolved in the aqueous solution per 100 parts of said quaternary ammonium compound.

The medium to long chain fatty acid of the water-soluble salt which is dissolved in the aqueous solution has a chain length from 7 to 23 carbon atoms and preferably from 8 to 18 carbon atoms. The water-soluble salt is preferably a salt of an alkali metal, in particular of lithium, sodium or potassium, but it may also be an ammonium salt. Suitable fatty acids are natural fatty acids such as caprylic acid, capric acid, lauric acid, myristic acid, palmitic acid, stearic acid, arachidic acid, behenic acid, palmitoleic acid, oleic acid, linoleic acid and linolenic acid or synthetic fatty acids such as odd fatty acids or branched fatty acids with chain length between 7 and 23 carbon atoms. Also mixtures of fatty acid salts can be used. The water-soluble salt can be introduced in the aqueous solution by adding the salt thereto or by generating the salt in the aqueous solution by adding precursor molecules, such as for instance the parent fatty acid and the corresponding alkali metal hydroxide. Other additives can also be added to the resulting liquid to enhance specific final product properties, e.g. glycerol, silica, carbonate, polyvinyl alcohol, colouring agents . . . .

The resulting liquid is highly suitable for drying. Drying can occur by different means as described already hereabove. Hot plate drying and spray drying appeared to be particularly suitable. With hot plate drying, a glass-like material is often obtained which can be easily handled and flaked into the desired final form. With spray drying, particles between 20 and 200 µm could be easily obtained in regular spray drying equipment, using nozzles or rotating disc atomizers. Larger particles can be obtained by spray granulation (wherein the dried particles are recycled together with fresh aqueous solution to the drying chamber until they have the desired size) or by spray agglomeration (wherein an adhesive is applied to the dried particles so as to form agglomerates). In contrast to U.S. Pat. No. 5,486,363, a dry product (which has a water content lower than 1%, preferably lower than 0.5%) can be obtained in one single step without having to use special long, narrow spray dryers.

Without the use of a water-soluble fatty acid salt, in particular the alkali metal fatty acid salt, problems of sticking and lumping are often observed during drying. Furthermore, the product is difficult to handle because of fast water absorption during cooling after the drying step. However, with the addition of the water-soluble fatty acid salt to the liquid feed, all operational difficulties could be avoided. Furthermore, the obtained product already exerted an important degree of free flowability but the stability under ambient conditions was still bad.

In accordance with the present invention, both the free-flowing behaviour and the stability under ambient conditions are strongly improved further by admixing at least one powdery salt of a medium to long chain fatty acid with a multi-valent counter ion to the solid product which is obtained after drying the aqueous solution and which has preferably a water content of less than 10 wt. %, preferably of less than 5 wt. % and more preferably of less than 3 wt. %.

The medium to long chain fatty acid of the powdery fatty acid has a chain length from 7 to 23 carbon atoms and preferably from 8 to 18 carbon atoms. The powdery salt is preferably a salt of an alkaline earth metal, in particular of magnesium or calcium although also other bivalent metal ions are possible, such as zinc, copper or cobalt or even trivalent metal ions such as for example iron. Suitable fatty acids are again natural fatty acids such as caprylic acid, capric acid, lauric acid, myristic acid, palmitic acid, stearic acid, arachidic acid, behenic acid, palmitoleic acid, oleic acid, linoleic acid and linolenic acid or synthetic fatty acids such as odd fatty acids or branched fatty acids with chain length between 7 and 23 carbon atoms. Also mixtures of fatty acid salts can be used. Moreover, other additives can be added simultaneously in order to attain particular final product characteristics as desired, known by people that are skilled by the art, e.g. silica powder, in particular fumed or fused silica, sulphates, carbonates, colouring agents, etc. Advantageously, 0.1 to 1.0 parts by weight, preferably 0.2 to 0.5 parts by weight of silica powder is admixed, per 100 parts by weight of said quaternary ammonium compound, to the dried solid product. In this way, compaction of the free-flowing powder in the hermetically sealed container (bag) wherein it is stored, could be avoided.

The powdery fatty acid salt has to be mixed in a powdery form with the dried solid product. Powder mixing can occur by different technologies with satisfying results: fluidized bed mixer, paddle mixer, tumble mixer, high shear mixer, etc. . . . The powdery salt is admixed to the dried solid product in an amount of at least 0.1 part by weight per 100 parts by weight of the quaternary ammonium compound. Preferably it is added thereto in an amount of at least 0.5 parts by weight, more preferably in an amount of at least 1.0 part by weight and most preferably in an amount of at least 1.5 parts by weight per 100 parts by weight of the deliquescent quaternary ammonium salt. In order to keep the content of the quaternary ammonium compound in the final product as high as possible, the powdery salt is preferably added in an amount of less than 10 parts by weight, more preferably less than 6 parts by weight and most preferably less than 4 parts by weight per 100 parts by of weight of the deliquescent quaternary ammonium salt.

The free-flowing powder has preferably an average particle size larger than 20 μm, preferably larger than 50 μm and more preferably larger than 100 μm but smaller than 1000 μm, preferably smaller than 800 μm and more preferably smaller than 600 μm. The average particle size is a volume average, i.e. 50 volume % of the particles have a size smaller than the average particle size whilst 50 volume % have a larger particle size. The advantage of larger particle sizes is that the same stability and free flowing properties can be achieved with less powdery fatty acid salt.

The product that was obtained using a suitable amount of the water-soluble fatty acid salt or salts at the drying step and a suitable amount of the powdery fatty acid salt or salts during the powder mixing step showed excellent free flowability and stability under ambient conditions. However, only the combination of these two salts as described above gave satisfactory results: the water-soluble fatty acid salt in dissolved state in the feed liquid in the drying step and the powdery metal salt mixed in dry form in a second step. When the fatty acid salt was omitted in one of the two steps, the product did not show the desired properties anymore. Even more, simply switching the order of addition of the two fatty acid salts, thus adding the multivalent metal fatty acid salt during the drying step and the univalent metal fatty acid salt during the mixing step, appeared to be detrimental to the final product quality.

The free-flowing powder obtained by the process according to the invention contains preferably at least 80 wt. %, more preferably at least 90 wt. % and most preferably at least 95 wt. % of quaternary ammonium salt. The powder is free-flowing so that it flows by gravity through a round orifice having a diameter of only 6 mm. It is moreover stable so that it preferably remains free-flowing when kept as a thin layer having a thickness of about 3 mm for 3 hours at 20° C. and a relative air humidity of 75%. It is stored in a hermetically sealed container, in particular in a hermetically sealed bag, so that it can be stored for a very long time without loosing its free-flowing properties.

The free-flowing powder can in particular be used to prepare a feed additive mixture. This feed additive mixture is obtained by mixing the free-flowing powder with other powders to achieve a so-called premix. The other powders may comprise vitamins, minerals, anti-oxidants, antimicrobial agents, anthelmintics, microbial supplements, oligosaccharides, enzymes, amino acids, acidifiers, flavors, odor control agents, pellet binders, flow agents, fats, carotenoids and carcass modifiers. The feed additive mixture usually comprises between 1 and 15 wt. % of the free-flowing powder of the present invention. The above mentioned other powders are described more into detail in:

National research Council (NRC), 1993, Nutrient Requirements of Fish, p. 3-37

National research Council (NRC), 1994, Nutrient Requirements of Poultry, Ninth Revised Edition, p. 3-18; and in National research Council (NRC), 1998, Nutrient Requirements of Swine, Tenth Revised Edisition, p. 74-99

These publications, and especially the different products given as examples of the additives, are incorporated herein by reference.

EXAMPLES

The flowability of the powders was measured by adding 200 ml to a funnel and measuring the time required to flow out of the opening (diameter 6 mm). Dry fine sand was used as a reference (33 seconds).

Stability of the product was observed by spreading 1 g of choline chloride in a 2 mm thin layer on an aluminum plate and storing it in a climate chamber at 20° C. and 75% relative humidity. This test should represent on a short time scale how the bulk product stored in an open bag would behave over a couple of days. When the same test was used for commercial choline chloride 60% on corn cobs (vegetable carrier) as a reference, the product became sticky already after 90 minutes.

Example 1

A mixture of 15 kg of 55% aqueous choline chloride and 125 g of sodium stearate was heated to 60° C. The solution was fed to a spray dryer (diameter 2 m, height 4.5 m, ingoing air 160° C.) through a fountain nozzle. The dry product was collected at the bottom of a cyclone and contained 0.6% water and 1.5% sodium stearate. The remainder was choline chloride. No deposits could be observed in the drying chamber, the cyclone or the rotary valves. The product was allowed to cool and 500 g was then added to a lab-scale Lödige mixer together with 10 grams of calcium stearate and 1 g of silica Sipernat® 22S. After mixing for 15 minutes, a nice free flowable powder was obtained that was free of lumps.

Particle size d50=70 μm (volume average)

Flowability=29 seconds

Stability: no lumping or water droplets could be observed in 5 h

Example 2

A mixture of 15 kg of 70% aqueous choline chloride, 80 g of sodium palmitate and 80 g of sodium stearate was heated to 95° C. The solution was fed to a spray dryer (diameter 2 m, height 4.5 m, ingoing air 200° C.) through a rotating disc atomizer. Via a separate air flow, silica Sipernat® 22S was injected directly to the dryer at a rate corresponding to 0.2% on the dry product. The dry product was collected at the bottom of the cyclone and mixed in a continuous fashion with 2% of calcium stearate in a paddle mixer. The average residence time in the mixer was approximately 8 minutes. The resulting powder was free of lumps and showed good free flowability.

Particle size d50=90 μm
Flowability=35 seconds
Stability: no lumping could be observed. Water droplets on the surface could only be observed after 3 h.

Example 3

A mixture of 15 kg of 55% aqueous choline chloride, 30 g of sodium palmitate and 90 g of sodium oleate was heated to 60° C. The solution was fed to a spray dryer (diameter 2 m, height 4.5 m, ingoing air 160° C.) through a fountain nozzle. The dry product was collected at the bottom of a cyclone and contained 0.7% water and 97.9% choline chloride. No deposits could be observed in the drying chamber, the cyclone or the rotary valves. The product was allowed to cool and 500 g was then added to a lab-scale Lödige mixer together with 15 grams of calcium stearate and 2 g of CaCO3. After mixing for 15 minutes, a nice free flowable powder was obtained that was free of lumps.
Particle size d50=72 μm
Flowability=30 seconds
Stability: no lumping or water droplets could be observed in 5 h Example 4

A mixture of 2 kg of 75% aqueous choline chloride, 20 g of glycerol and 20 g of sodium stearate was heated to 95° C. Then, the liquid was poured in a thin layer on a hot ceramic plate at 240° C. Solidification occurred very fast and a glass-like layer was formed on the plate. After two minutes, the plate was allowed to cool down to 40° C. and the dry choline was scraped from the surface to obtain coarse particles. 500 g of this material was grinded and sieved and subsequently mixed with 10 g of powderous calcium stearate and 1 g of silica Sipernat® 22S in a lab-scale Lödige mixer. The resulting powder had a water content of 1.1%.
Flowability=30 seconds
Stability: no lumping or water droplets could be observed in 5 h Example 5

A mixture of 4.2 kg of 60% aqueous glycine betaine, 6.5 g of sodium palmitate and 6.5 g of sodium stearate was heated to 50° C. The solution was fed to a spray dryer (diameter 2 m, height 4.5 m, ingoing air 160° C.) through a fountain nozzle. The dry product was collected at the bottom of a cyclone and contained 0.5% water and 98.9% glycine betaine. No deposits could be observed in the drying chamber, the cyclone or the rotary valves. The product was allowed to cool and 500 g was then added to a lab-scale Lödige mixer together with 7.5 grams of calcium palmitate and 7.5 grams of calcium stearate. After mixing for 15 minutes, a nice free flowable powder was obtained that was free of lumps.
Particle size d50=74 μm
Flowability=31 seconds
Stability: no lumping or water droplets could be observed in 24 h Comparative Example 6

An aqueous solution of 75% choline chloride was fed to a spray dryer (diameter 2 m, ingoing air 165° C.). The dry product was collected at the bottom of the cyclone and contained 1.2% water. The product came out mostly as lumps of material and was difficult to handle in subsequent process steps because of increasing stickyness. Furthermore, some deposits could be observed already after short drying operation in the cyclone and rotary valves.
Particle size: not measured
Flowability: not measured (lumps)
Stability: water droplets at the surface after 5 minutes; complete liquefaction after 30 minutes Comparative Example 7

To 10 kg of an aqueous solution of 55% choline chloride at 60° C., 120 g of sodium stearate and 165 g of calcium stearate were added. After mixing for 30 minutes with an ultraturrax mixer, a dispersion was obtained that was stable for at least a couple of hours. The dispersion was spray dried as explained in example 1. The product that was collected at the bottom of the cyclone was very lumpy and therefore particle size and flowability could not be measured. After milling the product, the resulting powder still showed too low flowability for measurement. Furthermore, the product already had clearly visible water droplets after 90 minutes in the stability test. This example shows the importance of the order of addition of the alkali and alkaline earth metal fatty acid salts.

Comparative Example 8a

An aqueous solution of 75% choline chloride was fed to a spray dryer (diameter 2 m, height 4.5 m, ingoing air 160° C.) through a rotating disc atomizer. No alkali metal fatty acid salt was added to the feed. In stead, calcium stearate was added in solid form directly to the drying chamber by means of an air flow. The flow of the calcium was dosed as such that 2.5% was obtained in the final product. The product was collected at the bottom of the cyclone and allowed to cool down. The product had the tendency to become a stone upon cooling.
Than, 500 g of the product was mixed in a lab-scale Lödige mixer together with 5 g of calcium stearate for 15 minutes. The water content of the final product was 0.5%.
Particle size d50=50 μm
Flowability: no flow
Stability: no water droplets could be observed in 5 h Comparative Example 8b 500 g of the powder obtained after drying in comparative example 8a, was mixed in a lab-scale Lödige mixer together with 7.5 g of sodium stearate for 15 minutes. The water content of the final product was 0.5%.
Particle size d50=50 μm
Flowability: no flow
Stability: no water droplets could be observed in 5 h
Both comparative examples 8a and 8b show the need of the alkali metal fatty acid salt to be present in dissolved state prior to drying.

Example 9

An aqueous solution of 75% choline chloride, heated to a temperature of 80° C. and containing 0.5% sodium stearate/palmitate (50:50) based on dry matter, was fed to a spray granulator by means of a nozzle. The liquid was sprayed into a stable bed of choline chloride particles and the material was dried in a hot air flow (ingoing air temperature 165° C.) in such a way that the fine particles are recovered at the top of the dryer from the outgoing air by means of a cyclone and then recycled to the bottom part in the dryer to maintain the bed. The heavy particles (granules) are removed from the bed by means of a particle classifier.

A first part of the resulting granules were tested as such in the climate chamber (Comp. Ex. 9a). A second part was additionally treated in a dry mixing step with 2% sodium stearate in solid form (Comp. Ex. 9b). A third part was treated in a dry mixing step with 2% calcium stearate in solid form (Ex. 9c).

A fourth sample (Comp. Ex. 9d) was prepared according to example 1 of NL6704009: a suspension of sodium stearate (20% based on dry matter) in 70% choline chloride aqueous solution was made by vigorously stirring at room temperature. The resulting milk was made to dryness on a hot plate. The resulting solid was milled before it was added to the climate chamber together with the three other samples.

When kept dry, samples 1, 2 and 3 were free-flowing. Sample 4 did not flow spontaneously through the funnel.

Major differences could further be observed in the stability test: samples 1, 2 and 4 already became sticky after 1 h and clearly showed water droplets on the surface after two hours, while sample 3 was rated as still free flowing after 5 h.

The invention claimed is:

1. A process for preparing a free-flowing powder containing, on a dry weight basis, per 100 parts by weight of the powder, at least 85 parts by weight of at least one deliquescent quaternary ammonium compound selected from the group consisting of choline chloride, choline bromide, choline hydroxide, choline carboxylate, choline carbonate, glycine betaine, and D,L-carnitine, wherein said process comprises drying an aqueous solution of said quaternary ammonium compound to achieve a solid product and by admixing at least one powdery salt of a medium to long chain fatty acid with a multivalent counter ion to said solid product in an amount of at least 0.1 part by weight per 100 parts by weight of said quaternary ammonium compound, and wherein, before drying said aqueous solution, at least one water-soluble salt of a medium to long chain fatty acid with a univalent counter ion is introduced into said aqueous solution, and at least 0.1 part by weight of said water-soluble salt is dissolved in said aqueous solution, per 100 parts by weight of said quaternary ammonium compound.

2. A process according to claim 1, wherein at least 0.2 parts by weight of said water-soluble salt is dissolved in said aqueous solution per 100 parts of said quaternary ammonium compound.

3. A process according to claim 1 or 2, wherein the aqueous solution is heated to a temperature higher than 50° C. to dissolve said water-soluble salt therein.

4. A process according to claim 1, wherein more than 20% of the water-soluble salt introduced in the aqueous solution is dissolved therein before drying the solution.

5. A process according to claim 1, wherein per 100 parts by weight of said quaternary ammonium compound, less than 10 parts by weight of said water-soluble salt is introduced in said aqueous solution.

6. A process according to claim 1, wherein said water-soluble salt introduced into the aqueous solution contains more than 50 wt. % of said quaternary ammonium salt.

7. A process according to claim 1, wherein per 100 parts by weight of said quaternary ammonium compound, at least 0.5 parts by weight of said powdery salt is admixed to said solid product.

8. A process according to claim 1, wherein per 100 parts of said quaternary ammonium compound, less than 10 parts by weight of said powdery salt is admixed to said solid product.

9. A process according to claim 1, wherein said quaternary ammonium compound comprises choline chloride.

10. A process according to claim 1, wherein the aqueous solution is dried by atomizing it into small droplets and by drying these droplets to produce dried particles, the aqueous solution being dried in particular dried by flash drying, fluidized bed drying or spray drying which also includes spray granulation and spray agglomeration.

11. A process according to claim 1, wherein said free-flowing powder contains, on a dry weight basis, per 100 parts by weight of the powder, at least 95 parts by weight of said deliquescent quaternary ammonium compound.

12. A process according to claim 2, wherein at least 0.4 parts by weight of said water-soluble salt is dissolved in said aqueous solution per 100 parts of said quaternary ammonium compound.

13. A process according to claim 3, wherein the aqueous solution is heated to a temperature higher than 75° C. to dissolve said water-soluble salt therein.

14. A process according to claim 4, wherein the more than 75% of the water-soluble salt introduced in the aqueous solution is dissolved therein before drying the solution.

15. A process according to claim 5, wherein per 100 parts by weight of said quaternary ammonium compound, less than 3 parts by weight of said water-soluble salt is introduced in said aqueous solution.

16. A process according to claim 6, wherein said water-soluble salt introduced into the aqueous solution contains more than 70 wt. % of said quaternary ammonium salt.

17. A process according to claim 7, wherein per 100 parts by weight of said quaternary ammonium compound, at least 1.5 parts by weight of said powdery salt is admixed to said solid product.

18. A process according to claim 8, wherein per 100 parts of said quaternary ammonium compound, less than 4 parts by weight of said powdery salt is admixed to said solid product.

19. A process for preparing a free-flowing powder containing, on a dry weight basis, per 100 parts by weight of the powder, at least 85 parts by weight of at least one deliquescent quaternary ammonium compound, wherein said process comprises atomizing into small droplets an aqueous solution of said quaternary ammonium compound, drying these droplets to produce dried particles and admixing at least one powdery salt of a medium to long chain fatty acid with a multivalent counter ion to said dried particles in an amount of at least 0.1 part by weight per 100 parts by weight of said quaternary ammonium compound, and wherein before atomizing said aqueous solution, at least one water-soluble salt of a medium to long chain fatty acid with a univalent counter ion is introduced into the aqueous solution; and at least 0.1 part by weight of said water-soluble salt is dissolved in said aqueous solution, per 100 parts by weight of said quaternary ammonium compound.

20. A process according to claim 19, wherein said quaternary ammonium compound is choline chloride.

* * * * *